(12) United States Patent
Hamel et al.

(10) Patent No.: US 7,001,333 B2
(45) Date of Patent: Feb. 21, 2006

(54) SURGICAL RETRACTOR SYSTEM

(76) Inventors: Ross J. Hamel, 293 Yorkminster Rd., West Chester, PA (US) 19382; James Velikaris, 4824 Rainbow Ridge Cir., Schwenksville, PA (US) 19473; Sean Kerr, 22 Briar Rd., Oreland, PA (US) 19075

(*) Notice: Subject to any disclaimer, the term of this patent is extended or adjusted under 35 U.S.C. 154(b) by 103 days.

(21) Appl. No.: 10/315,658

(22) Filed: Dec. 10, 2002

(65) Prior Publication Data
US 2003/0195392 A1 Oct. 16, 2003

Related U.S. Application Data

(63) Continuation-in-part of application No. 09/742,254, filed on Dec. 20, 2000, now Pat. No. 6,524,238.

(51) Int. Cl.
*A61B 1/00* (2006.01)
(52) U.S. Cl. .................... 600/242; 600/208
(58) Field of Classification Search ........ 600/201, 600/213, 210, 208, 226, 227, 235, 237, 242; 411/337, 356, 347; 606/104, 190
See application file for complete search history.

(56) References Cited

U.S. PATENT DOCUMENTS

| | | | |
|---|---|---|---|
| 2,588,169 A | 3/1952 | Shea | 32/19 |
| 4,337,762 A | 7/1982 | Gauthier | 128/20 |
| 4,608,972 A | 9/1986 | Small | 128/92 |
| 4,683,896 A | 8/1987 | Herbst et al. | 128/785 |
| 4,705,038 A | 11/1987 | Sjostrom et al. | 128/305 |
| 4,713,077 A | 12/1987 | Small | 623/16 |
| 4,765,328 A | 8/1988 | Keller et al. | 128/303 |
| 4,829,857 A | 5/1989 | Jones | 81/177 |
| 5,147,367 A | 9/1992 | Ellis | 606/96 |
| 5,190,549 A | 3/1993 | Miller et al. | 606/85 |
| 5,195,506 A | 3/1993 | Hulfish | 128/20 |
| 5,224,930 A | 7/1993 | Spaeth et al. | 604/33 |
| 5,339,802 A | 8/1994 | Cook | 128/20 |
| 5,380,291 A | 1/1995 | Kaali | 606/164 |
| 5,443,471 A | 8/1995 | Swajger | 606/99 |
| 5,445,641 A | 8/1995 | Frigg et al. | 606/86 |

(Continued)

FOREIGN PATENT DOCUMENTS

DE      1 034 322      7/1958

(Continued)

OTHER PUBLICATIONS

Leibinger catalog excerpt, pp. 10-11, trocar and drill guide, date not available.

*Primary Examiner*—David O. Reip
(74) *Attorney, Agent, or Firm*—Jones Day

(57) ABSTRACT

The present invention provides an improved surgical retractor system useful for holding tissue away from a surgical site during a medical or dental procedure. In one embodiment, the surgical retractor system is comprised of a tubular member, such as a cannula, and a retractor member. In an embodiment, the retractor member may be ring shaped. The retractor member preferably may have an opening therethrough for receiving the cannula. An engaging member associated with the retractor member may be provided for rotatably engaging the cannula. In one embodiment, the cannula may have external threads that are releaseably engaged with the engaging member and allows the degree or amount of tissue retraction to be adjusted. The cannula may be configured to be used with and secured to a handle to facilitate using the retractor system. A method of using the retractor system is also disclosed.

37 Claims, 14 Drawing Sheets

U.S. PATENT DOCUMENTS

| | | | |
|---|---|---|---|
| 5,507,801 A | 4/1996 | Gisin et al. | 606/86 |
| 5,512,037 A | 4/1996 | Russell et al. | 600/206 |
| 5,586,991 A | 12/1996 | Yoon | 606/185 |
| 5,618,309 A | 4/1997 | Green et al. | 606/207 |
| 5,707,390 A | 1/1998 | Bonutti | 606/204 |
| 5,716,325 A | 2/1998 | Bonutti | 600/204 |
| 5,746,743 A | 5/1998 | Greenberg | 606/96 |
| 5,755,721 A | 5/1998 | Hearn | 606/96 |
| 5,807,338 A | 9/1998 | Smith et al. | 604/164 |
| 5,817,110 A | 10/1998 | Kronner | 606/148 |
| 5,843,039 A | 12/1998 | Klemm | 604/164 |
| 5,851,216 A | 12/1998 | Allen | 606/185 |
| 5,888,196 A | 3/1999 | Bonutti | 600/204 |
| 5,948,000 A | 9/1999 | Larsen et al. | 606/232 |
| 5,951,561 A | 9/1999 | Pepper et al. | 606/80 |
| 5,957,927 A | 9/1999 | Magee et al. | 606/99 |
| 5,957,947 A | 9/1999 | Wattiez et al. | 606/185 |
| 5,980,493 A | 11/1999 | Smith et al. | 604/164 |
| 5,984,865 A | 11/1999 | Farley et al. | 600/213 |
| 5,989,259 A | 11/1999 | Penenberg et al. | 606/99 |
| 5,993,470 A | 11/1999 | Yoon | 606/185 |
| 6,004,326 A | 12/1999 | Castro et al. | 606/99 |
| 6,013,083 A | 1/2000 | Bennett | 606/104 |
| 6,083,225 A | 7/2000 | Winslow et al. | 606/61 |
| 6,110,179 A | 8/2000 | Flivik et al. | 606/99 |
| 6,113,605 A | 9/2000 | Storer | 606/99 |
| 6,132,435 A | 10/2000 | Young | 606/104 |
| 6,206,826 B1 | 3/2001 | Mathews et al. | 600/210 |
| 6,238,435 B1 | 5/2001 | Meulink et al. | 623/22.12 |
| 6,425,859 B1 | 7/2002 | Foley et al. | 600/204 |
| 6,524,238 B1 | 2/2003 | Velikaris et al. | 600/213 |

FOREIGN PATENT DOCUMENTS

| | | |
|---|---|---|
| DE | 44 16976 A1 | 11/1995 |
| DE | 298 09 038 U1 | 9/1998 |

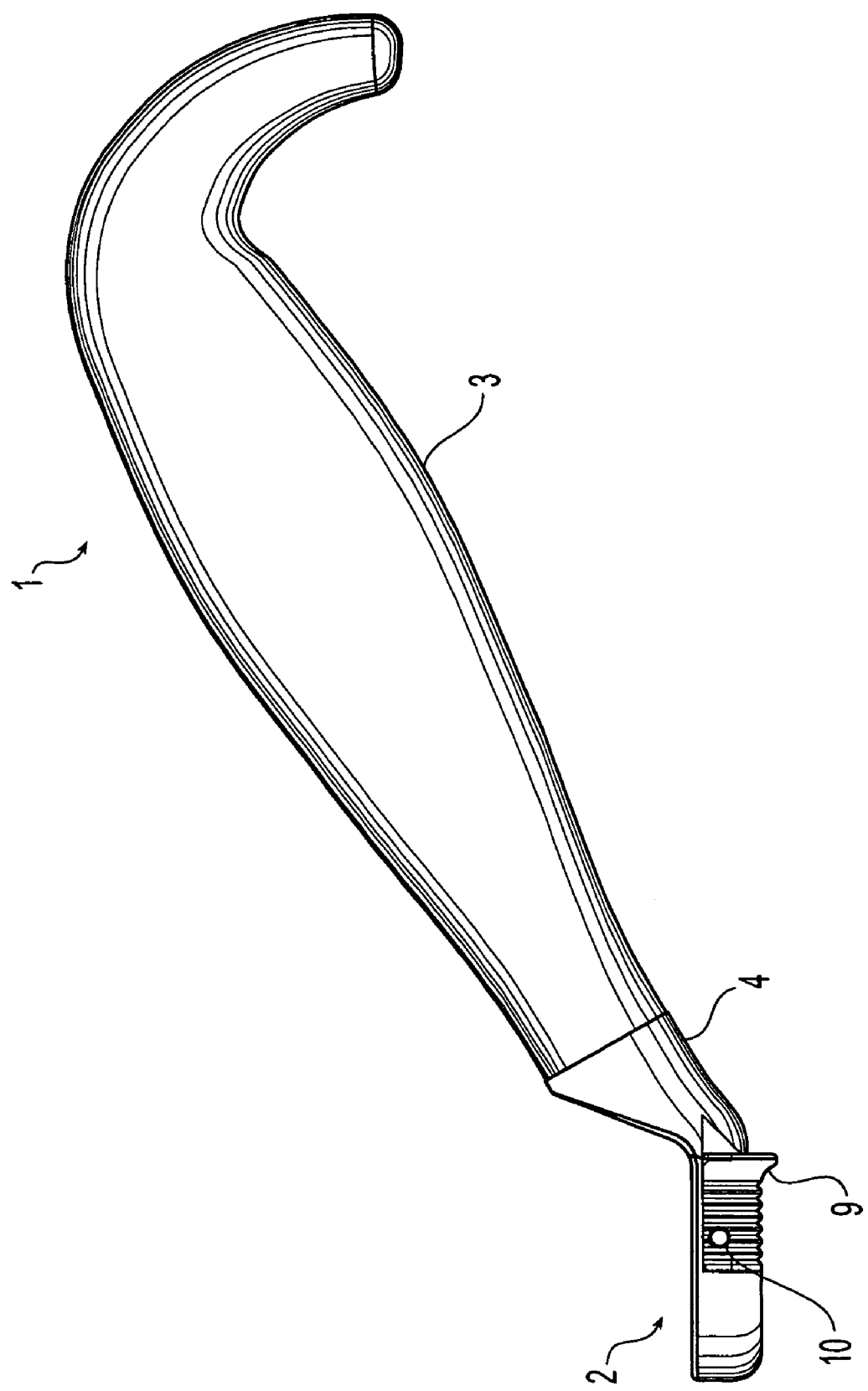

SURGICAL RETRACTOR SYSTEM

CROSS-REFERENCE TO RELATED APPLICATIONS

This is a continuation-in-part of U.S. patent application Ser. No. 09/742,254 filed Dec. 20, 2000 U.S. Pat. No. 6,524,238, entitled "Universal Handle," which is incorporated herein by reference.

BACKGROUND OF THE INVENTION

The present invention generally relates to surgical instruments used in surgical procedures, and more particularly to an improved handle that permits various instruments to be releaseably attached for quicker and easier interchange.

The development of newer minimally invasive surgical techniques, such as laparoscopic surgery, have allowed surgeons to successfully perform numerous operative procedures in many instances which in the past required the need for large surgical incisions. In this newer procedure, one or several very small incisions are made in the patient through which various surgical instruments may be used to perform the required surgical procedure. Minimally invasive surgery offers benefits which include creating less trauma to the patient, reducing the risk of post-operative infections, and allowing speedier recovery than conventional surgery with its larger incisions.

Trocars are commonly used in minimally invasive surgeries. They generally consist of a hollow cannula (tube) and an obturator (bladed or pointed piercing device) which are used, in combinat ion, to make a small portal into a patient. The obturator is designed to slide inside the cannula to create a single unit that may be used to penetrate a small incision that has been previously made by a surgeon. Once the trocar has penetrated the patient's body cavity, the obturator is withdrawn while leaving the cannula in position. Various surgical instruments can then be worked through the cannula to perform whatever surgical technique is required.

Trocars are particularly useful in many types of surgery in which a small incision will permit the required surgical procedure to be completed. One such application is in maxillofacial surgery where bone fractures occurring in the maxilla or mandible are stabilized by bone screws and/or bone plates. In this trocar application, drill guides can be inserted through the cannula which allow the surgeon to pre-drill holes in the bone for receiving bone screws. Trocars can also be used with soft tissue retractors, such as cheek retractors which are employed to hold the tissue away from the surgical site so that it does not interfere with fixation of the facial fracture.

The can may be fastened or secured to a handle of some type. This helps the surgeon control the trocar and facilitates the process of both making the initial incision accurately and subsequently working with various instruments in a manner which reduces the chance of the cannula being pulled from the patient's body cavity prematurely.

Handles of the past have typically employed various approaches for coupling the can to the handle. For example, cannulas were often attached in a permanent manner to the handle such as by welding. Semi-permanent type couplings have also been used such as threading the cannula head to the handle, or providing set screws to hold both parts together. U.S. Pat. No. 5,755,721 to Hearn discloses another semi-permanent type of coupling wherein a retaining ring with an internal depression around its circumference is provided that mates with a spring and ball detent on a surgical instrument. The instrument is pushed into the retaining ring until the detent is seated in the depression.

The handle designs of the past have several drawbacks. The permanent type attachment does not allow the surgeon to interchange different kinds or sizes of surgical instruments. This reduced flexibility for the surgeon and increased prices for each trocar unit which must contain both a handle and permanently affixed can. Overall inventory costs are thereby also increased.

Although the semi-permanent type couplings offer interchangeability of surgical instruments, they too have been problematic. Using set screws or threaded coupling of the can to the handle makes changing instruments cumbersome, especially when it must be done during the exigencies of a surgical procedure. While offering improvement, the coupling described in the Hearn patent does not positively lock the cannula to the handle in a manner that requires the surgeon to unlock the cannula from the handle.

Accordingly, there is a need for a handle which allows for improved releaseability and interchangeability of various surgical instruments with the handle while overcoming the problems associated with the foregoing prior art devices.

Retractor members, which in some embodiments may be ring-shaped, may be used to withdraw or hold soft tissue away from a surgical site to prevent injury to the tissue not directly affected by the surgical procedure. For example, a retractor member is sometimes used in maxillofacial medical and dental procedures to retract the cheek of a patient to repair jaw bone fractures by drilling holes in the damaged bone and implanting bone screws, sometimes in combination with bone plates. Retractor members may be mounted on a tubular member, such as a can. The can may be inserted through an incision in the patient's cheek and the retractor member is inserted through a second or other bodily opening, such as the mouth or second incision, and then affixed onto the cannula. The can/retractor member combination, however, has proven difficult for the surgeon to assemble and adjust in situ during the surgical procedure.

BRIEF SUMMARY OF THE INVENTION

The invention is generally directed to a handle and system of surgical tools which can be designed specifically to be compatible and interchangeable with the handle.

In accordance with one embodiment, the handle is comprised of a grasping portion and a handle lock assembly. The grasping portion is used by the surgeon to hold and control the handle. The handle lock assembly comprises a body with a top and a bottom, and further includes a retractable slider pin which secures a surgical instrument to the handle.

In another embodiment, the lock assembly body includes an opening disposed in the body through which surgical instruments are inserted. The opening, which is preferably circular in one embodiment, extends from the top to the bottom of the lock assembly body creating an opening passing completely through the body. The retractable slider pin is movable from an extended position in which the pin protrudes into the opening and secures the surgical instrument to the handle, to a retracted position in which the pin is withdrawn from the opening.

The slider pin may be connected to a handle slider which is preferably a rectangular or square block in configuration, but is not limited to those shapes. The slider pin may be integrally connected with the handle slider such as by welding or the slider pin and handle slider may be formed as an integral unit. Also preferably, the handle slider is slidably mounted in a cavity or other opening provided in the body of the handle lock assembly. Alternatively, the handle slider may be mounted on the exterior of the handle lock assembly which is a matter of design choice.

In one embodiment, the handle lock assembly of the handle includes at least one handle release. The handle release is used to move the retractable slider pin from the extended position to the retracted position as discussed above. The handle release is connected to the handle slider which is connected to the slider pin, thereby moving the pin.

In accordance with another embodiment, at least one biasing member is provided which biases the slider pin toward its extended position. Preferably, the biasing member is a helical spring. In one embodiment, the biasing member may be held by a recess provided in the handle slider. The handle lock assembly may be attached to the grasping portion of the handle by welding. The handle including the grasping portion and handle lock assembly may be made of stainless steel, however, it may be made of any material suitable for the intended application. The grasping portion of the handle may be hollow which reduces the cost and weight of the handle.

In accordance with one embodiment, the surgical instrument that may be used with the handle of the invention is a can or trocar assembly. The can, or different instrument as the case may be, may include indentations which are designed to engage the retractable slider pin thereby securing the cannula to the handle. Preferably, the cannula or different instrument may further include additional depressions which may be used to secure at least one additional surgical device to the handle. In one embodiment, a soft tissue retractor is an additional device that may be attached to the handle. Preferably, the cannula or different instrument, and additional devices that may be attached to the handle may be made of stainless steel, however, they may be made of any material suitable for the intended application. The can or different instrument may further include a body portion and a head portion, and preferably where these two portions are of different size diameters, an inclined ramp may be included between the two portions to facilitate insertion of the can into the handle as discussed below. The can or different surgical instrument may further comprise a knob connected to the cannula or different instrument for grasping and rotating the cannula or different instrument. At least one slot may be provided in the knob for mating and engaging with at least one tab provided on a surgical instrument intended to be inserted through the cannula or different surgical instrument secured to the handle to prevent rotation of the inserted instrument in the cannula or different instrument. An obturator or a drill guide which are well known in the art may be such an instrument provided with at least one tab which mates with the at least one slot in the knob of the can or different instrument.

In another embodiment, the handle lock assembly body of the handle may include a transition portion between the handle lock assembly and the grasping portion. The grasping portion preferably may be angularly displaced, preferably about 30 degrees, from the plane of the top of the handle lock assembly.

A handle lock system for performing a surgical procedure is also provided. The system may comprise a handle which has a grasping portion and handle lock assembly. The lock assembly comprises a body with a top and a bottom, and a retractable slider pin. The system further may include a can or different instrument having indentations to engage the slider pin thereby securing the cannula to the handle. In one embodiment, the handle lock system may further include additional depressions for securing an additional surgical instrument to the trocar handle. Preferably, the additional surgical instrument may be a soft tissue retractor.

A method of interchangeably using surgical instruments in a handle lock assembly, and a trocar specifically, is also provided, which may comprise the steps of: (a) providing a handle, the handle having a grasping portion and a lock assembly, the lock assembly comprising a body with a top and a bottom, a retractable slider pin, and a passageway disposed in the body wherein the surgical instruments are inserted for securing to the handle, the retractable slider pin being movable from an extended position in which the pin protrudes into the passageway to a retracted position in which the pin is withdrawn from the passageway; (b) providing a cannula having indentations to engage the retractable slider pin thereby securing the cannula to the handle; (c) inserting the cannula in the handle; (d) locking the cannula to the handle by engaging the retractable pin in one of the indentations; (e) retracting the retractable pin from the extended position to the retracted position; and (f) removing the cannula from the handle. The method may comprise inserting a different surgical instrument having indentations into the passageway other than a cannula. The method may further include inserting an obturator into the cannula.

In another embodiment of the method, locking the cannula or different surgical instrument to the handle may further include the steps of withdrawing the slider pin from the passageway to the retracted position by a user and inserting the cannula or different instrument into the passageway before the slider pin engages one of the indentations. The method may also further include the step of rotating the cannula or different instrument to align the indentations and sliding pin to lock the cannula or different instrument to the handle.

The present invention provides an improved surgical retractor system useful for holding tissue away from a surgical site during a medical or dental procedure. In one embodiment, the surgical retractor system is comprised of a tubular member, such as a cannula, and a retractor member. In an embodiment, the retractor member may be ring shaped. The retractor member preferably may have an opening therethrough for receiving the cannula. An engaging member associated with the retractor member may be provided for rotatably engaging the cannula. In one embodiment, the cannula may have external threads disposed on at least a portion thereof that are rotatably and releaseably engaged with the engaging member and allows the degree or amount of tissue retraction to be adjusted. The cannula may be configured to be used with and secured to a handle to facilitate using the retractor system.

In accordance with one embodiment, the tubular member preferably has threads and the engaging member of the retractor member engages the threads on the tubular member to adjust the position of the retractor member along the axial length of the tubular member. The engaging member may be disposed in a bore in the retractor member that extends from the retractor member's outer surface to and in communication with the opening in the retractor member which receives the tubular member.

In an embodiment, the engaging member may have a blunted tip protruding at least partially into the opening of the retractor member for engaging the external threads of the tubular member. In another embodiment, the engaging member may comprise a screw and the retractor member may have a threaded hole communicating with the opening of the retractor member for receiving the tubular member. The screw preferably is disposed in the threaded opening. In yet another embodiment, the engaging member comprises threads disposed on the retractor member adjacent the opening for receiving the tubular member, and the threads of the retractor member are engageable with the threads of the tubular member. In another embodiment, the engaging member is a pin.

In one embodiment, the tubular member is a cannula. In another embodiment, the retractor member is shaped substantially like a ring. The retractor member may have at least one hole configured to be engaged by at least part of a surgical instrument or tool for manipulating the retractor member.

A cheek retractor system is provided which may comprise a cannula having threads disposed on at least a portion of the cannula, a retractor member having an opening therethrough for receiving the cannula, and an engaging member associated with the retractor member. The engaging member may rotatably engage the cannula. In one embodiment, the cannula comprises a distal end and a proximal end. A window may be provided at the proximal end of the cannula. The window may be used for facilitating observation and/or irrigation of the surgical site.

In one embodiment, the retractor member has a top surface, a bottom surface, and a side surface. The retractor member may further comprise at least one hole extending at least partially through the side surface for engaging part of a surgical instrument or tool used to manipulate the retractor member. In another embodiment, at least two such holes may be provided for engaging a surgical instrument or tool. A hole extending from the top surface to the bottom surface of the retractor member may also be provided for manipulating the retractor member.

A system for retracting tissue is provided comprising a cannula having an external surface and an axial length. At least a portion of the cannula may have external circumferential threads. A retractor member may be included in the system and have an opening configured to receive the cannula therethrough, and an engaging member associated with and protruding at least partially into the opening for engaging the threads on the cannula. The retractor member may be adjustable along the axial length of the cannula.

A handle may also be provided with the system which is configured to releasably secure the cannula to the handle. The handle may have a retractable slider pin for securing the cannula to the handle. The cannula may have a circumferential groove configured and adapted to engage the slider pin. In one embodiment, the cannula may be capable of being rotated while being secured to the handle. In another embodiment, the groove prevents the cannula from moving axially along its longitudinal length while the pin is engaged with the groove.

A method of retracting tissue for a surgical procedure is provided comprising the steps of: providing a cannula having a distal end and a proximal end; providing a retractor member having an opening therethrough for receiving the cannula, the retractor member having an engaging member for engaging the cannula; inserting the cannula through a first bodily opening; inserting the retractor member through a second bodily opening; guiding the distal end cannula into the opening of the retractor; and rotating the cannula or the retractor member to engage the retractor member and the cannula. The tissue may be adjustably withdrawn from the distal end of the cannula. In one embodiment, the retractor member and the cannula are rotatably engaged. In another embodiment, the method further comprises the cannula having an external surface with circumferential threads disposed on at least a portion of the external surface and the retractor member further comprises threads disposed on a surface of the retractor member surrounding the opening for receiving the cannula. In one embodiment, the cannula is rotated to threadably engage the retractor member and the cannula. In another embodiment, the retractor member is rotated to threadably engage the retractor member and the cannula. In another embodiment, the first bodily opening is an incision in the tissue of a patient and the second bodily opening is a second incision in the tissue of a patient. In yet another embodiment, the first bodily opening is an incision in the tissue of a patient and the second bodily opening is the mouth of a patient.

A retractor kit is also provided comprising: a cannula having external threads on at least a portion thereof and a retractor member having an opening configured and adapted to receive the cannula. The retractor member may have an engaging member that is engageable with the external threads of the cannula. The kit may also include a handle having a grasping portion and a handle lock assembly for holding the cannula. Rotation of the tubular member or the retractor member rotatably engages the retractor with the tubular member. An obturator may also be provided in one embodiment that is configured and adapted to be inserted into the cannula.

It will be appreciated that the tissue retractor is particularly useful for maxillofacial surgical procedures. However, use of the tissue retractor is not limited to maxillofacial surgery alone and it may be used with and in any type of medical or dental procedure where it is desirable to releaseably attach medical or dental instruments to a handle.

BRIEF DESCRIPTION OF THE DRAWINGS

The features and advantages of the present invention will become more readily apparent from the following detailed description of the invention in which like elements are labeled similarly and in which:

FIG. 1 is a side elevation view of the handle of the present invention;

DETAILED DESCRIPTION OF THE INVENTION

Referring to FIG. 1, the handle 1 is depicted in one embodiment as including a handle lock assembly 2 and a grasping portion 3. Handle lock assembly 2 may include a transition portion 4 connected to grasping portion 3 as shown; however, lock assembly 2 may be attached directly to grasping portion 3 with minimal or no transition depending on the shape and design of the handle 1 desired. It will further be readily apparent that the shape of the grasping portion 3 is a matter of ergonomic design choice and is not limited to the embodiment shown. Furthermore, grasping portion 3 may be formed of one or more pieces secured together in any manner commonly used in the art (e.g., welding, set screws, etc.) and may be either solid or hollow. It will also be appreciated that the size, shape, and position of the lock assembly 2 on the grasping portion 3 is a matter of design choice and is similarly not limited to the preferred embodiment shown.

Figure 2A:
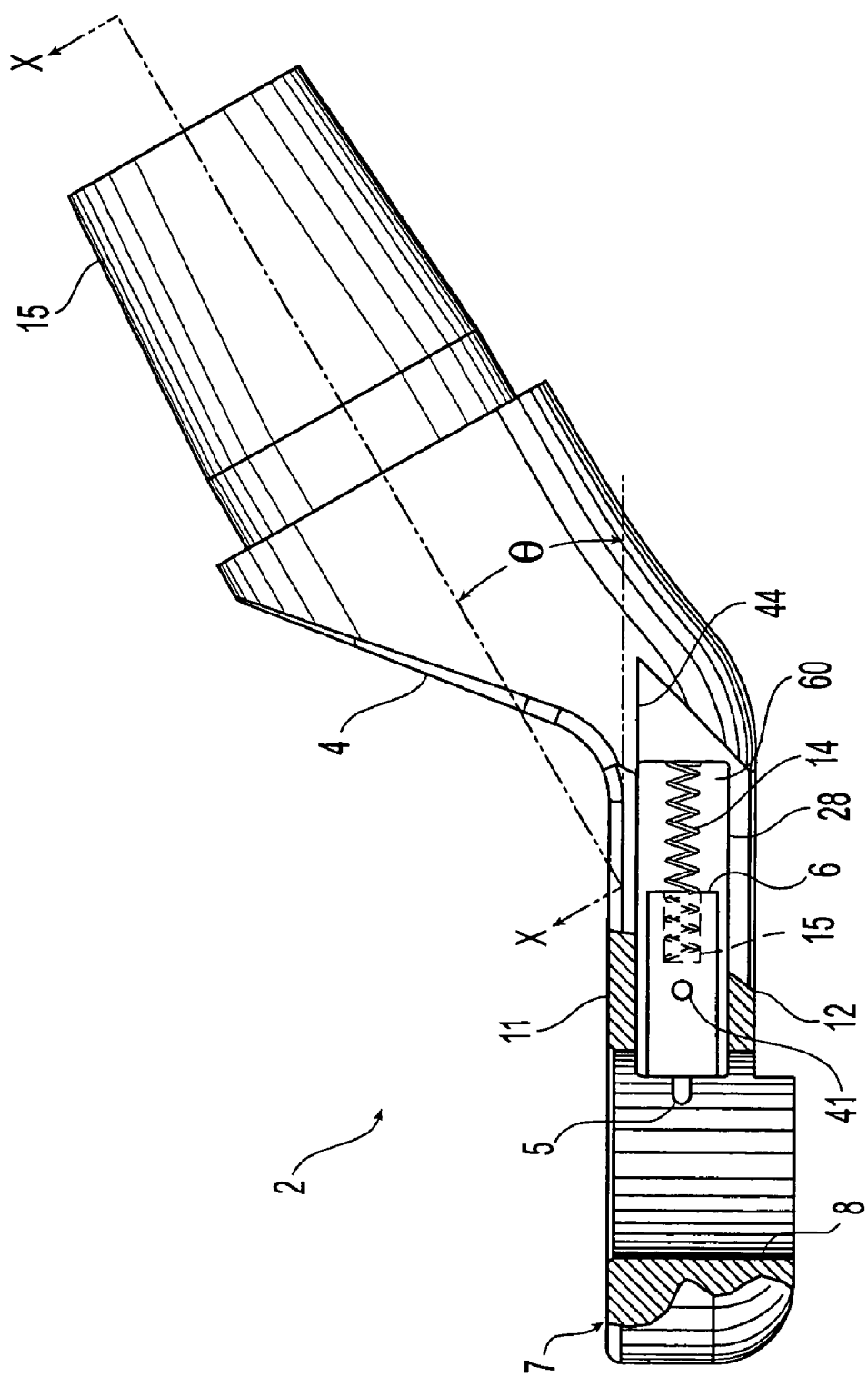
FIG. 2A is a side elevation view of the handle lock assembly of the handle of FIG. 1 shown with the handle release removed.
Figure 2B:
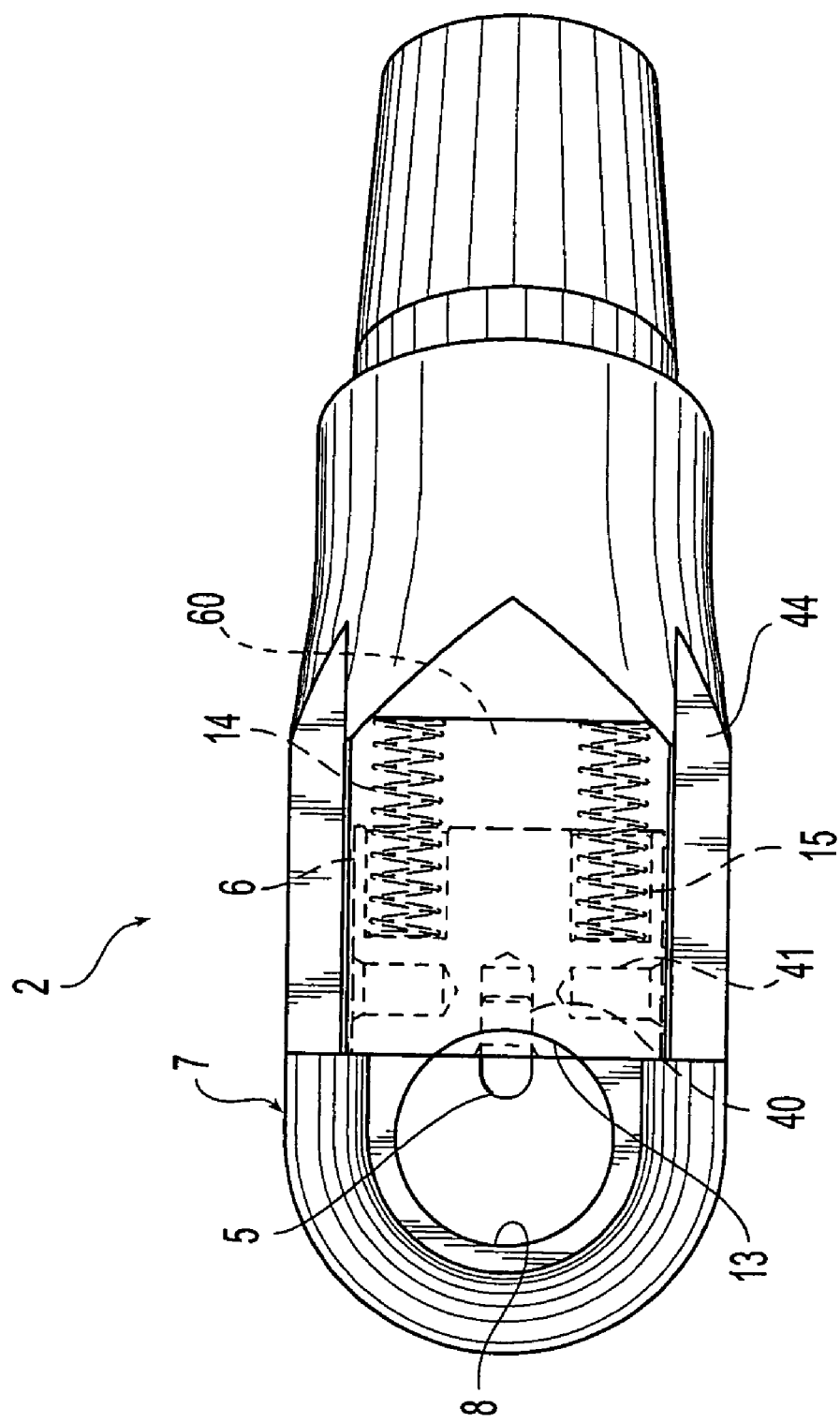
FIG. 2B is a bottom plan view of the handle lock assembly of the handle of FIG. 1 shown with the handle release removed.
Figure 2C:
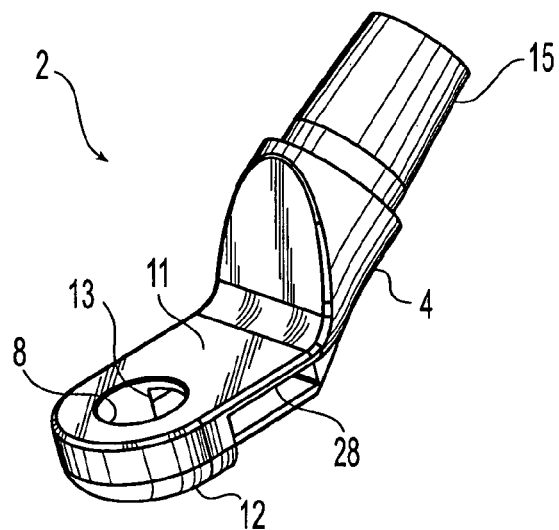
FIG. 2C is an isometric view of the handle lock assembly of the handle of FIG. 1 shown with the handle release removed.
Figure 2D:
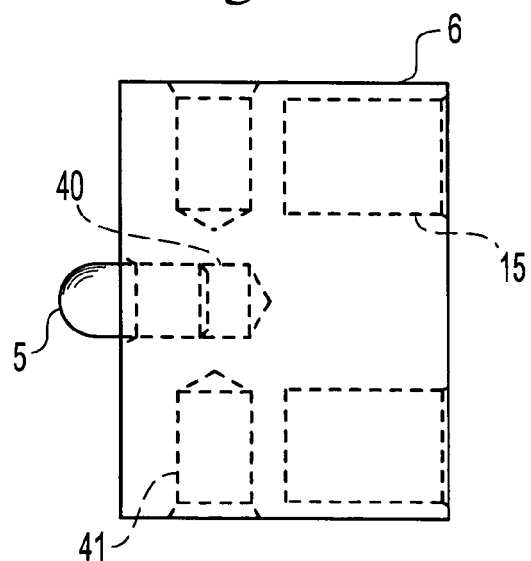
FIG. 2D is a plan view of the handle slider of the handle lock assembly of the handle of FIG. 1.
Figure 2E:
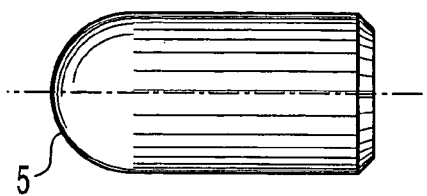
FIG. 2E is a view of the slider pin of the handle lock assembly of the handle of FIG. 1.

FIGS. 2A–2G depict the handle lock assembly 2 of the handle 1 in more detail (for clarity, the same numerical designations are used for same parts in every figure contained herein). Referring to FIG. 2A, the handle lock assembly 2 comprises a body 7, a retractable slider pin 5, and a handle slider 6 which is slidably mounted within a cavity provided in body 7. Preferably, handle slider 6 is a rectangular or square block in which various recesses have been made to accommodate other components of the handle lock assembly 2 (best seen in FIG. 2D). Pin 5 (FIG. 2E) is rigidly connected to handle slider 6, preferably by press fitting the pin into recess 40 provided in slider 6 (FIG. 2D). Alternatively, the pin 5 may be attached to the handle slider 6 in any manner commonly known in the art, and may in fact be an integral part of the slider 6 formed during manufacture of the slider. Pin 5 as shown preferably has rounded edges to facilitate engaging the indentations provided in surgical instruments as will be described below.

Figure 2F:
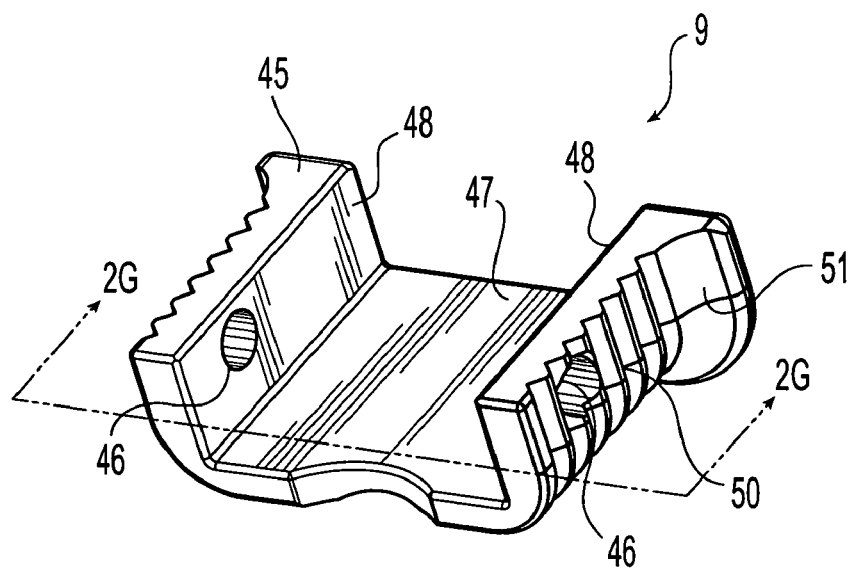
FIG. 2F is an isometric view of the handle release of the handle lock assembly of the handle of FIG. 1.
Figure 2G:
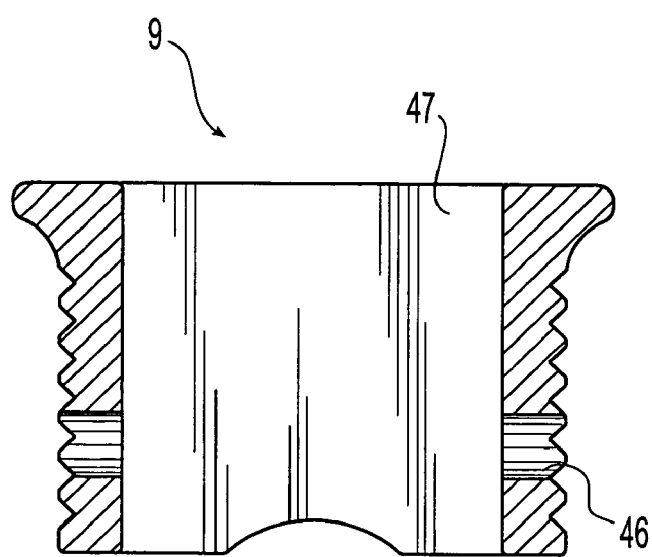
FIG. 2G is a top cross-sectional view of the handle lock assembly of the handle of FIG. 1.

Referring to FIG. 1 and best seen in FIGS. 2F & 2G, a sliding handle release 9 is provided in the preferred embodiment shown which is U-shaped and wraps around the bottom of the handle lock assembly body 7. Handle release 9 has a base 47 with sidewalls 48 projecting upwards and connected to the base. In one embodiment shown, handle release 9 has a flattened surface 45 which mates with and slides on a flat landing 44 (FIG. 2B) formed or machined on the body 7 of the handle lock assembly 2. Handle release 9 may be attached to each side of the handle slider 6 in any number of ways commonly used in the art. For example, the handle release 9 may be attached to the handle slider 6 with press-fit dowel pegs 10 as shown or with set screws (not shown) which fit into recesses 41 provided in the handle slider 6 (FIG. 2D) and pass through openings 46 in each side of the handle release 9. Preferably, the handle release 9 also has a ribbed or other non-slip surface 50 which will allow the surgeon to securely grip the release. A flange 51 also may be provided to assist gripping and retracting handle release 9. Although handle release 9 is depicted as U-shaped, the handle release is not limited to this embodiment and any shape or number of handle releases may be employed, the shape and number being a matter of ergonomic and/or design preference.

The handle lock assembly body 7 of handle lock assembly 2 may further contain an opening 8, preferably circular as depicted, extending completely through the body from the top 11 to the bottom 12 (FIGS. 2A and 2C). Retractable slider pin 5 protrudes into opening 8 in the body 7 through a side window 13 formed or cut into the side of the opening (best seen in FIG. 2C). This position is referred to as the "extended" position of the retractable slider pin 5.

As shown in FIG. 2C, the body 7 of the handle lock assembly 2 in one embodiment contains a transition portion 4 as discussed above and a handle attachment end 15 for connecting the handle lock assembly 2 to the grasping portion 3 (see also FIG. 1). Preferably, the attachment end 15 may be configured for welding to the grasping portion 3 as depicted, but is not limited in that regard. Thus, the handle lock assembly 2 may be connected to grasping portion 3 in any suitable manner commonly known in the art including semi-permanent connections such as threading the lock assembly to the handle grasping portion, the use of screws, fasteners, etc. Preferably, the attachment end 15 comprises a tapered cylindrical end designed to be inserted into a hollow handle grasping portion 3 which may be permanently connected to the handle lock assembly 2 by welding. As explained above, the handle lock assembly 2 may be designed with a minimal or no transition portion 4 of any type, the transition portion being strictly a matter of design choice. Moreover, enumerable possible shapes for the body 7 of handle lock assembly 2 and accompanying means of attaching the body to the grasping portion 3 are possible as will be evident without departing from the invention described herein; the shape and attachment means being a matter of design choice.

As shown in FIG. 2A, the gripping portion 3 may be angularly displaced from the plane of top 11 of the handle lock assembly body 7 as measured by an angle θ between the top 11 and a longitudinal centerline axis X—X drawn through the transition portion 4 (see FIG. 2B). Angle θ is preferably 0 degrees to 90 degrees, most preferably about 30 degrees. However, it will be readily apparent that angle θ may be varied to whatever angle is desired and necessary depending upon the particular intended surgical application and the configuration of the body 7, transition portion 4, and grasping portion 3 of the handle 1.

In one embodiment shown in FIGS. 2A and 2B, biasing members, which in this embodiment comprise springs 14, are provided within the handle lock assembly body 7 to hold the handle slider with retractable slider pin 5 in the "extended" position wherein the pin protrudes into the circular opening 8. The springs 14 may be confined on one end within recesses 15 (best seen in FIG. 2D) made in the handle slider 6. The other end of the springs 14 may contact the interior wall of the handle lock assembly body 7 located opposite the recesses 15.

The surgeon operates the handle lock assembly 2 by moving the handle release 9 in a direction which retracts the pin 5 from the circular opening 8 against the force of the springs 14. This position is referred to as the "retracted" position of the retractable slider pin 5. When the surgeon releases the handle release 9, the retractable slider pin 5 is automatically returned to its initial "extended" position (i.e., protruding into circular opening 8) by the springs 14. It will be appreciated that the present invention may be constructed with other forms of biasing members and with only one spring or any number of springs, the number and type of biasing members being strictly a matter of design choice.

Although helical springs are depicted, it will further be appreciated by those skilled in the art that the invention is not limited with regard to the style, size, or spring force constant (k) of the spring or springs that are used which will depend on the particular intended application. For example, leaf springs, torsion springs, cantilevered bending members, and other biasing members may be used. A spring force (k) should be selected which is sufficient to positively hold the retractable slider pin 5 in the "extended" position described above (i.e., the pin extending into the circular opening 8) to securely hold the cannula or other surgical instrument in the handle, while at the same time not being so great that it would be unduly difficult for the surgeon to retract the pin to the "retracted" position for changing or rotating the cannula or other surgical instrument. The springs 14 may be made of any suitable material commonly used for such members, and for the intended application of the device shown should be suitable for a surgical device. It should also be noted that the design of the recesses 15 provided in the handle slider 6 may be varied in any number of ways to accommodate the specific number, size, and style of biasing members employed. Alternatively, the springs 14 may engaged with the handle slider 6 or body 7 by other means commonly known in the art with and without the use of any recesses 15 whatsoever. For example, the body 7 may contain the recesses or other means to hold the springs 14.

Figure 3A:
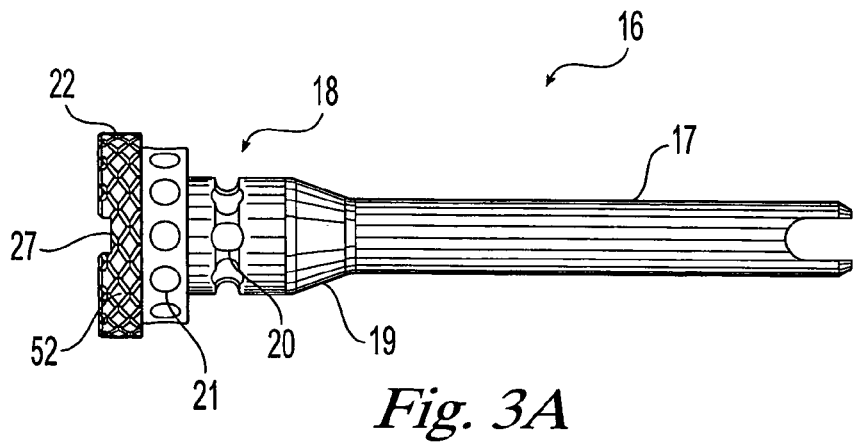
FIG. 3A is a plan view of a cannula which may be used interchangeably with the handle 1 of FIG. 1.
Figure 3B:
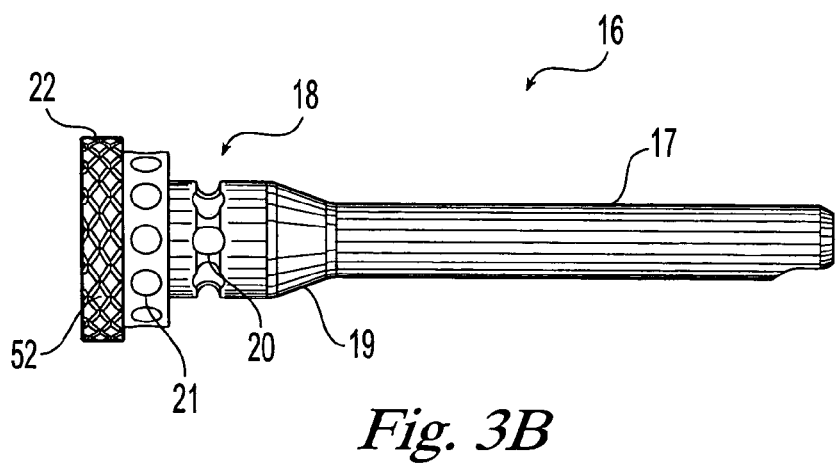
FIG. 3B is a 90 degree rotated plan view of the cannula of FIG. 3A.

The operation of the handle will be further understood by reference to FIGS. 3A and 3B which depict a cannula that may be used with the invention. Cannula 16 is a hollow tube-like structure that has a circular cross section comprising a body portion 17 and a head portion 18. In one embodiment, an inclined ramp portion 19 is provided which transitions the preferably smaller diameter body portion 17 to the larger diameter head portion 18. The shape of the ramp portion 19 causes the retractable slider pin 5 to automatically retract when the surgeon pushes the cannula 16 through the circular opening 8 of the handle lock assembly 2, the body portion 17 of the cannula being inserted first through the circular opening 8. This conveniently allows the cannula 16 to be inserted into the handle lock assembly 2 without the surgeon having to use the handle release 9. However, it should be noted that no ramp portion 19 is necessary with the present invention which is not limited in that regard. Accordingly, the body portion 17 and the head portion 18 may be of the same diameter and the surgeon would use the handle release 9 to insert the cannula 16 into the handle lock assembly 2, as explained more fully below, and then release the handle release to lock the cannula into position.

Still referring to FIGS. 3A and 3B, the cannula, or other surgical instrument designed to be used with the handle 1 may be provided with locking indentations 20. The indentations 20 may be provided around the circumference of the head portion 18 as shown to mate with the retractable slider pin 5 of the handle lock assembly (FIG. 2A). The shape and size of the locking indentations 20 may vary and are configured to mate with the retractable slider pin 5. In operation, the retractable slider pin 5 engages one of the locking indentations 20 when the cannula 16 is in position after it has been inserted through the circular opening 8 of the handle lock assembly 2 (FIG. 2A). Preferably, the retractable slider pin 5 mates with the indentations 20 in a manner so that the cannula 16 is positively locked in the handle 1 and cannot be inadvertently dislodged or withdrawn. Preferably, in order to remove or rotate the cannula, or other surgical instruments that may be used, the surgeon takes the positive step of using the handle release 9 to first retract the retractable slider pin 5. A knob 22 is formed on the end of head portion 18 of the cannula 16 and provides a structure for the surgeon to grasp while inserting or rotating the cannula. Preferably, the knob 22 has a knurled or similar non-slip surface 52.

Operation of the handle 1 of the present invention is best described by reference to FIGS. 2A, 2B, and 3A. The surgeon first selects the proper size cannula 16 for the particular surgical procedure involved. Cannula 16 having ramp portion 19 is inserted in the circular opening 8 in the handle lock assembly 2 of handle 1 until the retractable slider pin 5 engages one of the locking indentations 20 of the cannula, thereby locking the cannula in the handle. In this scenario, the ramp portion 19 causes pin 5 to automatically retract as described above by inserting the cannula into the handle 1. Alternatively, if a cannula 16 is used that does not have a ramp portion 19 (i.e., the diameter of the cannula body portion 17 equals the diameter of the head portion 18), the surgeon preferably first moves the sliding handle release 9 to retract pin 5 before inserting the cannula in the handle 2. After the cannula 16 is inserted in the handle 1, handle release 9 is released by the surgeon so that pin 5 engages one of the locking indentations 20 thereby locking the cannula into the handle. This latter procedure of using the handle release 9 to retract pin 5 while inserting a cannula 16 may also be used with a cannula that has a ramp portion 19. Depending on the circumferential alignment of the retractable slider pin 5 with the locking indentations 20 when the cannula is inserted into the handle 1, it may be necessary to turn knob 22 on the head portion 18 of the cannula 16 to rotate the cannula until the pin and one indentation properly align and are engaged.

To remove cannula 16 from the handle 1, the surgeon moves the sliding handle release 9 to retract pin 5 and then withdraws the cannula. The handle release 9 may also be used in this same fashion to rotate a cannula 16 while it is inserted in the handle 1 if the surgeon prefers a different rotational position for the cannula.

Figure 4A:
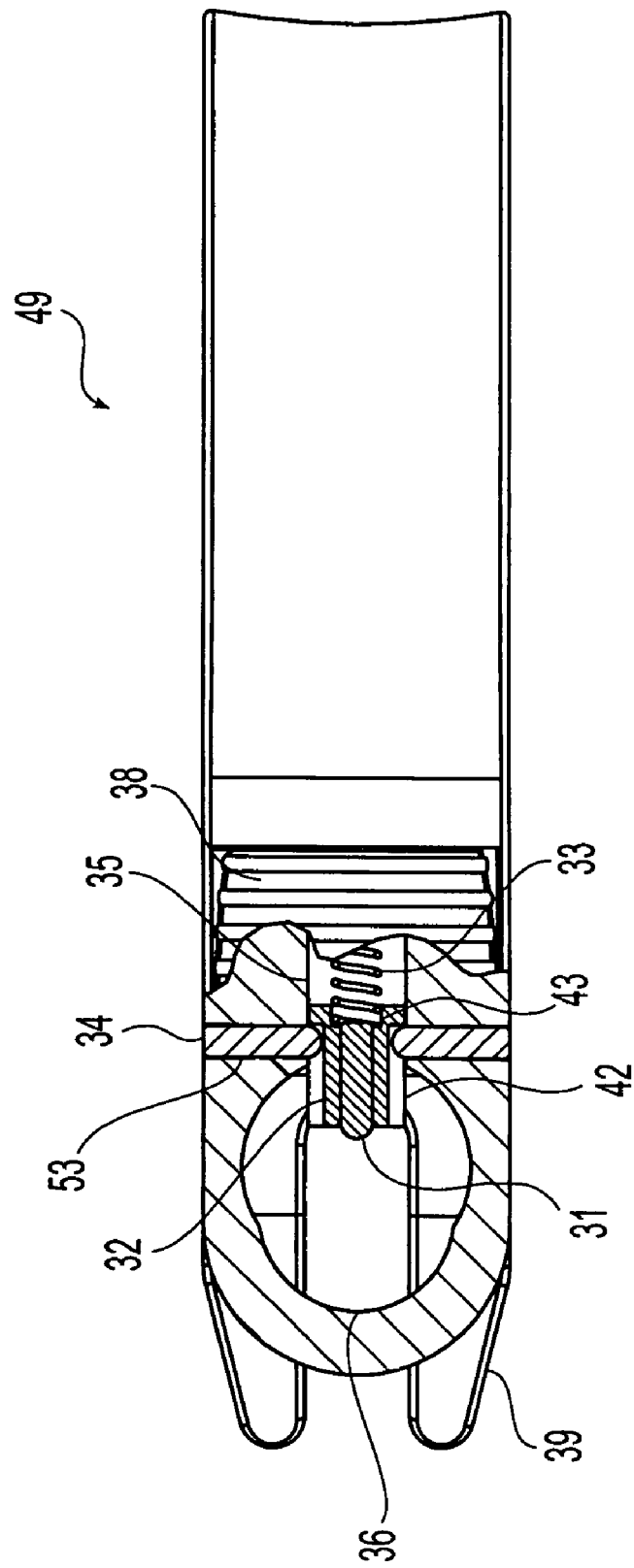
FIG. 4A is a top plan view of a soft tissue C-retractor which may be used with the handle of FIG. 1 shown with the sliding C-retractor releases partially removed.
Figure 4B:
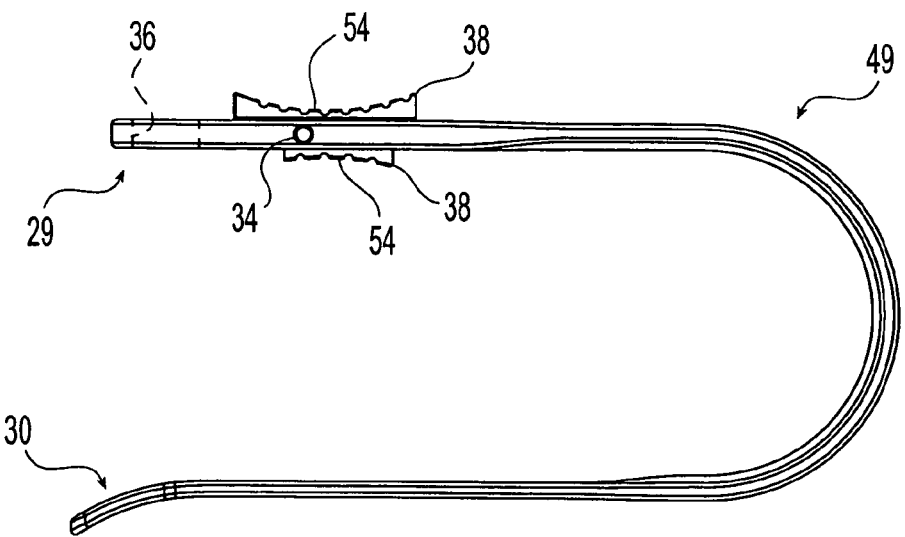
FIG. 4B is a side elevation view of a soft tissue C-retractor which may be used with the handle of FIG. 1.
Figure 4C:
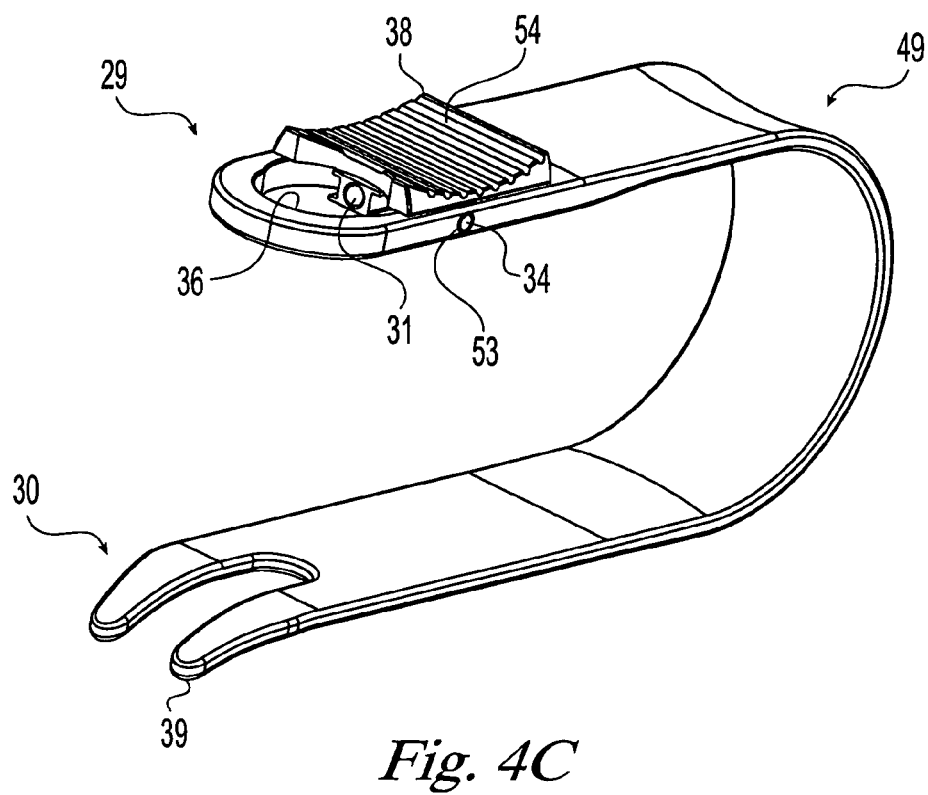
FIG. 4C is an isometric view of a soft tissue C-retractor which may be used with the handle of FIG. 1.

The cannula 16 in the embodiment shown in FIGS. 3A and 3B may preferably be provided with accessory depressions 21 which allow other surgical devices to be attached to the cannula which may utilize projections designed to mate with the depressions 21, thereby locking the devices to the cannula. One such device is a soft tissue retractor, such as cheek C-retractor 49 as shown in FIGS. 4A–4C, which is commonly used in maxillofacial surgery. The cheek retractor is often used for surgery involving the mandible or jawbone near the ear. In FIG. 4A, the cheek retractor 49 in one embodiment includes locking end portion 29 on one end of the C-retractor and a forked end portion 30 on the opposite end. Locking end portion 29 further comprises a retractable slider projection 31, a projection-carrying slider 32, at least one biasing member which preferably is a spring 33 as shown, and press-fit dowel pegs 34. An opening 36, preferably circular or oval, is also provided in locking end portion 29 along with an open keyway 35, preferably rectangular. Both opening 36 and keyway 35 extend completely through the locking portion 29. Also preferably, the open keyway 35 intersects the opening 36 to form a single contiguous opening wherein sits the retractable slider projection 31, projection-carrying slider 32, and spring 33. The projection 31 may be attached to the slider 32 in any manner commonly known in the art, and may in fact be an integral part of the slider formed during manufacture of the slider.

Still referring to FIGS. 4A–4C, the retractable slider projection 31 is held in an "extended" position by the spring 33 whereby the projection protrudes into opening 36. One end of spring 33 rests in a recess 43 provided in the rear of projection-carrying slider 32 while the other end of the spring contacts the back wall of keyway 35. The spring force of spring 33 should be selected to provide sufficient force to hold projection 31 into the "extended" position, while at the same time the force should not be so great that it would be unduly difficult for the surgeon to retract the projection. At least one groove or channel 42 may be provided in one or both sides of projection-carrying slider 32 which is closed at the rear near the spring 33. Press-fit dowel pegs 34 may be furnished which ride in the groove or grooves 42 and pass through openings 53 in the sides of the locking end portion 29. Alternatively, set screws or other means well known in the art may be used in lieu of dowel pegs 34. The dowel pegs 34 serve to hold the projection-carrying slider 32 in the locking end portion 29 of the C-retractor 49 by contacting the closed end of grooves 42 to prevent the spring 33 from pushing the projection-carrying slider into opening 36.

As best seen in FIGS. 4B and 4C, preferably two sliding C-retractor releases 38 may be provided for retracting slider projection 31 against the force of spring 33 to a "retracted" position whereby the projection is withdrawn from opening 36 into keyway 35. The retractor releases are attached to the top and bottom of projection-carrying slider 32 by an means commonly known in the art and may in fact be an integral part of the slider 32 formed during the manufacture of the slider. When the releases 38 are in place, the releases serve as a closure for the top and bottom of keyway 35. The retractor releases 38 preferably have a ribbed or other non-slip surface 54 which may be readily gripped by the surgeon. The retractor releases 38 may also be contoured and shaped to assist a surgeon in retracting the slider projection 31.

The forked end portion 30 of the C-retractor 49 includes two prongs 39; preferably, the prongs are curved away from the C-retractor 49 as shown. Alternatively, the shape of prongs 39 may be straight.

Use of the cheek C-retractor 49 can best be explained by reference to FIGS. 3A and 4A–4C. After the cannula 16 of handle 1 has been inserted through a patient's cheek, the forked end portion is inserted through a patient's mouth such that the body portion 17 of the cannula (inside the mouth) becomes situated between the two prongs 39. The locking end portion 29 is then affixed to the handle 1 (which is outside the patient's mouth) by using the sliding retractor releases 38 to retract projection 31, slipping opening 36 of the C-retractor 49 over knob 22 on the back of the cannula head portion 18 until the retractable slider projection 31 of the C-retractor aligns with one of the accessory depressions 21 of the cannula, and then releasing the releases 38 to engage the projection in one of the accessory depressions. The C-retractor is thereby secured to the handle 1. The slider projection 31 may also be retracted while the C-retractor 49 remains in position on the handle 1 in order to rotate the C-retractor to a number of positions around and in relation to the handle that may be desired by the surgeon.

Figure 5:
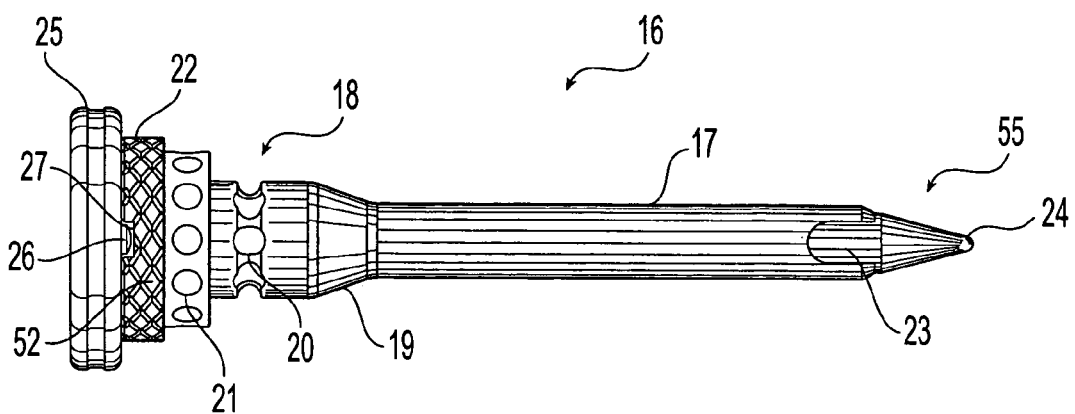
FIG. 5 illustrates the cannula of FIGS. 3A & 3B with an inserted obturator which may be used with the handle of FIG. 1.

Numerous surgical instruments can also be inserted and used through the cannula 16. Referring to FIG. 5, for example, an obturator 55 which is commonly used in minimally invasive surgical procedures is shown as being inserted in the cannula 16. The obturator in the embodiment depicted consists of a solid round shaft 23 (partially visible at the distal end of the cannula body portion 17) with a conically pointed tip 24 at one end and an enlarged, round head 25 at the opposite end. The shaft 23 is rigidly attached to head 25 in any manner commonly known in the art, such as by welding, set screws, threaded attachment, etc. In the embodiment shown, the obturator head 25 has at least one tab 26 which is designed to mate with at least one slot 27 provided in the knob 22 of cannula 16. This prevents the obturator 55 from rotating once it has been inserted through the cannula 16. Drill guides (not shown) which are also commonly employed in surgery for fracture fixation may also be used with the cannula 16 of handle 1. These drill guides may be designed to be compatible for use with cannula 16 and may also include at least one tab on a enlarged, round head like the obturator 55 which mates with at least one slot 27 provided in the knob 22 of the cannula.

Figure 6:
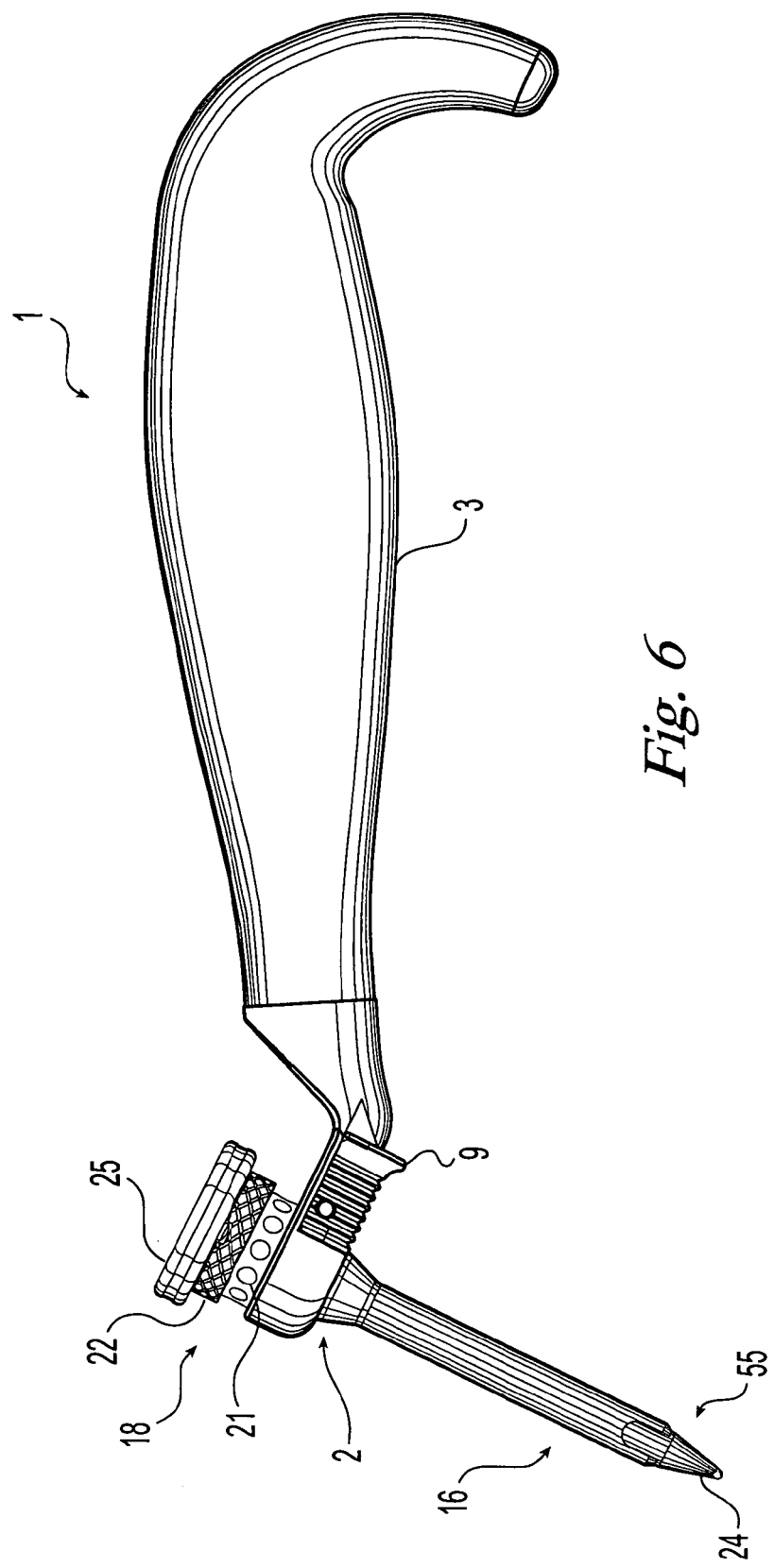
FIG. 6 is a side elevation view of the handle of FIG. 1 with an inserted cannula and obturator.
Figure 7:
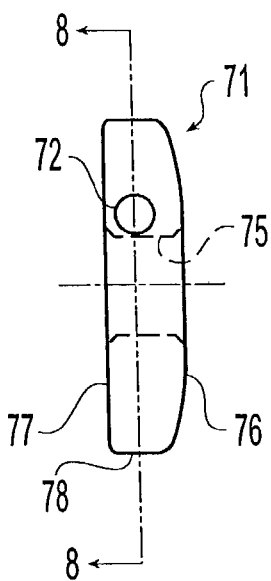
FIG. 7 is a side elevation view of a tissue retractor member which may be used with a cannula that may be used interchangeably with the handle of FIG. 1.

FIG. 6 depicts a fully assembled handle 1 with a cannula 16 inserted and locked in place by the handle lock assembly 2. An obturator 55 is shown inserted in the handle 1 with its pointed tip 24 protruding from the end of the cannula 16 and the obturator's enlarged, round head 25 visible at the opposite end of the cannula.

A tissue retractor system comprising a tubular member, preferably a cannula, with a mating tissue retractor member that is rotatably and releasably engageable with the cannula is shown in FIGS. 7–20. The retractor member may be used, for example, as a cheek retractor which is commonly employed in maxillofacial surgical procedures to hold the soft cheek tissue away from an operative site on the jaw bone where drilling, implantation of bone screws, and/or other procedures are occurring. In the embodiment shown in the foregoing referenced drawings, the retractor member and cannula may be used with the handle 1 disclosed herein; however, use of the retractor member and cannula are not limited in this regard and the retractor member and cannula may be used with handles of other design.

Referring to FIGS. 7–10, a retractor member 71, having an outer periphery that is preferably disk-like or circular in shape, has a top surface 76, a bottom surface 77, and side surface 78. Other shapes may also be used for the retractor member. An opening 75, also preferably circular in shape and preferably located near the center of the retractor member 71, extends through the retractor member 71 from the top surface 76 to the bottom surface 77 for receiving a cannula, such as, for example, the cannula 90 shown in FIGS. 14 and 15. The overall shape of the retractor member 71 is preferably ring shaped. A chamfer 79 (best seen in FIG. 9) may be provided at the transition from the top surface 76 and bottom surface 77 of the retractor member 71 to the central opening 75. The size of the opening 75 is preferably cooperatively sized with a cannula 90 to be used with and inserted through the retractor member 71, as explained in detail below.

In one embodiment, a ring-shaped retractor member 71 has an outer diameter of about 17 mm with an opening 75 of about 7 mm in diameter.

Figure 8:
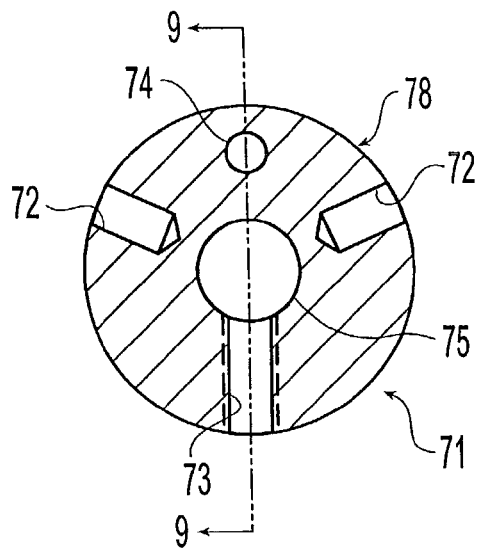
FIG. 8 is a cross-sectional top view of the tissue retractor member of FIG. 7.
Figure 9:
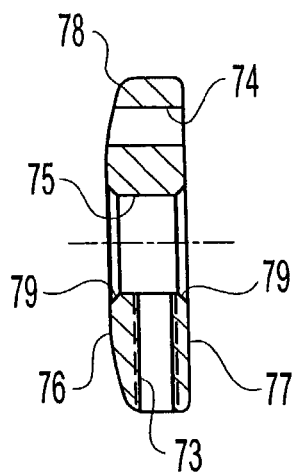
FIG. 9 is a cross-sectional side view of the tissue retractor member of FIG. 7.
Figure 10:
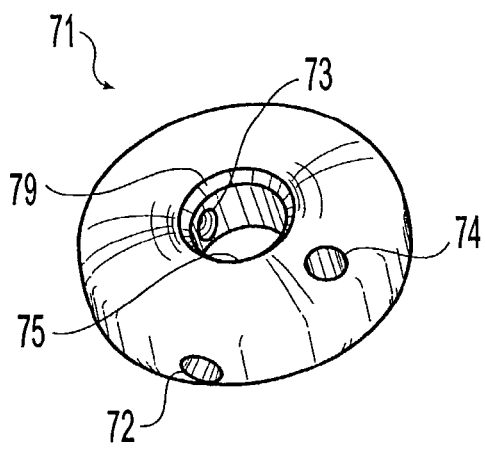
FIG. 10 is an isometric view of the tissue retractor member of FIG. 7.

One or more holes may be provided in the retractor member 71 to allow a surgeon to hold the retractor member 71 with a surgical instrument including, but not limited to forceps, hooks, or surgical pliers. In one embodiment shown in FIGS. 7–10, holes 72 may be provided through the side surface 78 of the retractor member 71 to receive the two prongs of a forceps (not shown), for example, to hold the retractor member 71. Preferably, at least two holes 72 are provided. The holes 72 may extend partially through the retractor member 71, as shown in FIG. 8, without intersecting the central opening 75. Alternatively, the holes 72 may be deep enough to intersect the opening 75.

A hole 74 may also be provided that passes from the top surface 76 to the bottom surface 77 of the retractor member 71, as shown, for assisting with the insertion and retrieval of the retractor member from a patient. For example, a hook may be inserted in hole 74 to prevent the retractor member from rotating while the ring is threaded onto the cannula 90. A hook may also be used in hole 74 to retrieve the retractor member 71. Alternatively, a suture may be fastened through hole 74 to assist with retrieving the retractor member 71. The uses for the foregoing holes are described below.

Figure 14:
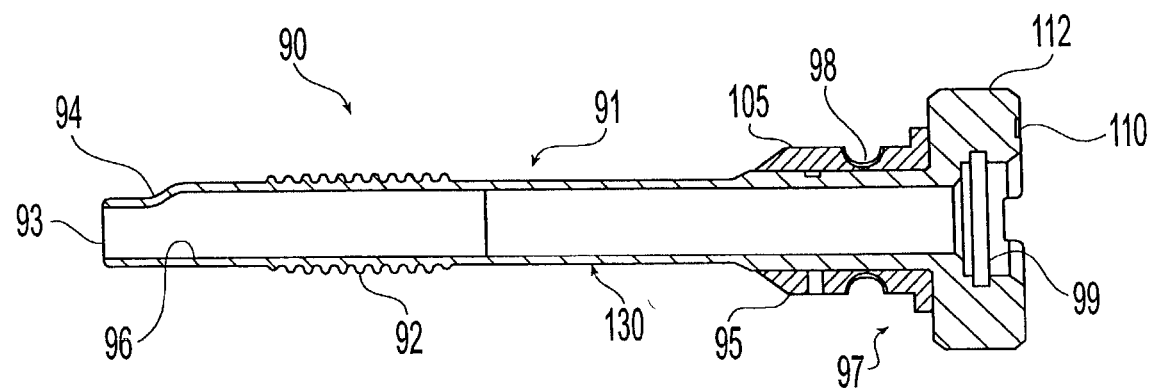
FIG. 14 is a cross-sectional side view of a cannula that may be used with the tissue retractor member of FIG. 7.
Figure 15:
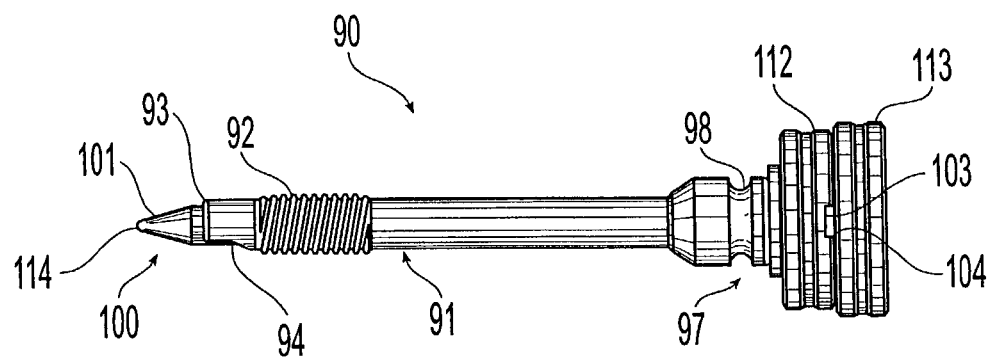
FIG. 15 is a side elevation view of a cannula that may be used with the tissue retractor member of FIG. 7.
Figure 16:
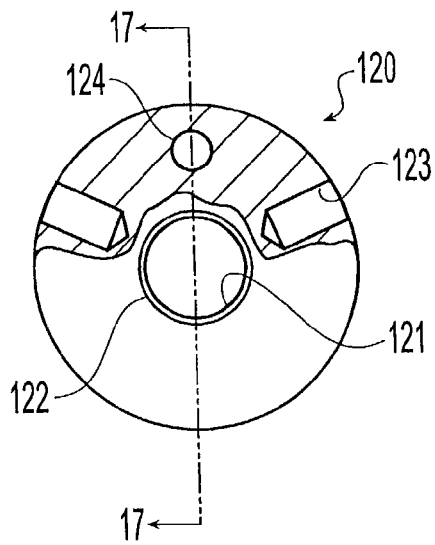
FIG. 16 is a partial cross-sectional top view of a tissue retractor member having a threaded opening.
Figure 17:
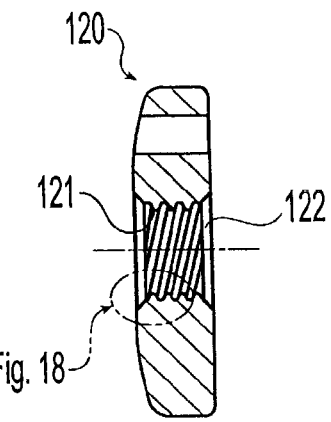
FIG. 17 is a cross-sectional side view of the tissue retractor member of FIG. 16.
Figure 18:
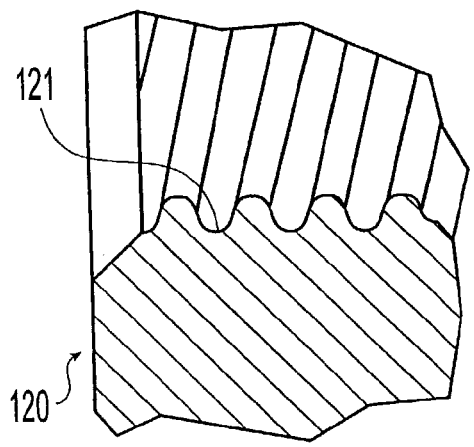
FIG. 18 is a cross-sectional partial side view of the threads of the tissue retractor member of FIG. 16.
Figure 19:
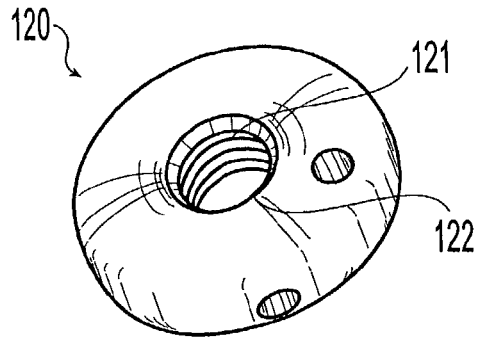
FIG. 19 is a isometric view of the tissue retractor member of FIG. 16.

One embodiment of a cannula 90 that may be used with the retractor member 71 is shown in FIGS. 14 and 15. Cannula 90 comprises a body portion 91 and a head portion 97. In one embodiment, the cannula 90 is provided with an inclined ramp portion 95 (whose function is described above in connection with FIGS. 3A and 3B) which transitions the preferably smaller diameter body portion 91 to the preferably larger diameter head portion 18. However, it will be appreciated that a ramp portion 95 is not necessary for operation of the retractor member 71 and cannula 90, and hence need not be provided.

The cannula 90 may preferably be secured to the handle 1 via a retractable slider pin 5 (see, e.g., FIGS. 2A, 2B, and 2E) associated with the handle 1 and that engages the cannula. In the embodiment shown in FIGS. 14 and 15, the head portion 97 of the cannula 90 includes a circumferential channel or groove 98 to engage a slider pin 5 (not visible in FIGS. 7–10) and to secure the cannula 90 to the handle 1. The groove 98 is configured and adapted with the pin 5 to allow the cannula 90 to be rotated with the cannula inserted in the handle 1, but also to preferably prevent the cannula from moving axially with respect to the handle 1. The groove 98 is preferably formed in an enlarged boss or portion 105 provided towards the proximal end 110 of the cannula 90.

It should be noted that many types of design approaches may be used to secure a cannula to a handle, and the handle and/or cannula is not limited to the use of retractable slider pins in that regard.

The cannula 90 has a longitudinal internal passage 96 that extends from a proximal end 110 (closest to the surgeon) to a distal end 93 (farthest from the surgeon and nearest the surgical site). The longitudinal passage 96 defines a longitudinal axis through the cannula 90. Passage 96 is preferably circular in cross-sectional shape and allows various surgical instruments (e.g., obturators, drill bits, etc.) and implants (e.g., bone screws, etc.) to be inserted through and used with the cannula 90.

The proximal end 110 of the cannula 90 may have a knob 112. Knob 112, which may be provided with a textured or knurled surface (best seen in FIG. 15) to facilitate grasping by the surgeon, may be used to rotate the cannula 90 as explained below.

The proximal end 110 of the cannula 90 may have a snap ring 99 (see FIG. 14) for securing other surgical instruments, such as an obturator, drill guide, or drill, for example, to the cannula 90.

The distal end 93 of the cannula 90 may have a window 94 that is used to observe and/or irrigate the surgical site while drilling holes and installing screws in the bone.

At least part of the body portion 91 of the cannula 90 preferably has external threads 92 for rotatably and releasably engaging an engaging member 80 associated with the opening 75 of the retractor member 71. The engaging member 80 preferably rotatably and releaseably engages the cannula 90. The threads 92 are preferably rounded, but are not limited in that regard. The external threads 92 may be located anywhere along the length of the cannula and is a matter of design choice. Accordingly, the invention is not limited in that regard.

Figure 11:
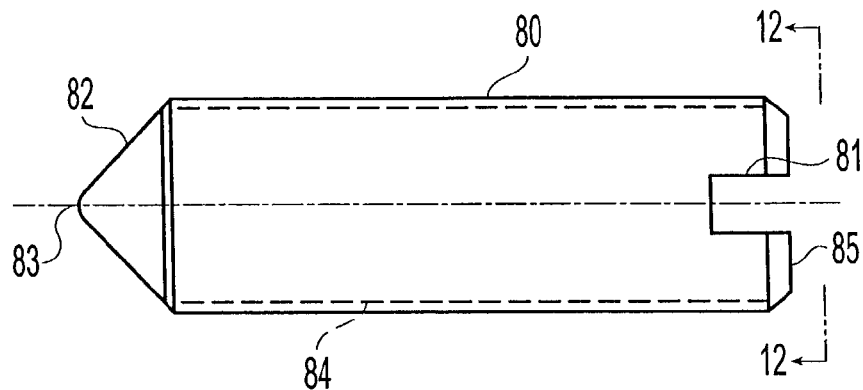
FIG. 11 is a side view of a screw that may be used with the tissue retractor member of FIG. 7.
Figure 12:
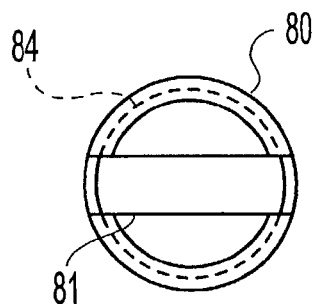
FIG. 12 is an end view of the screw of FIG. 11.
Figure 13:
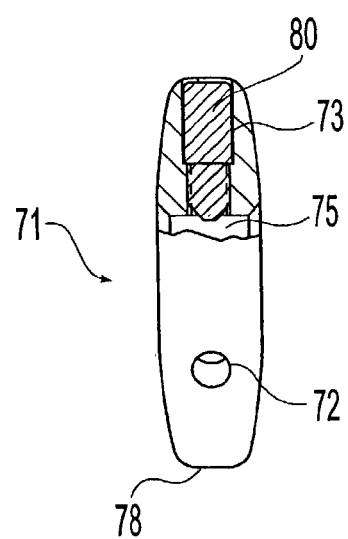
FIG. 13 is a partial cross-sectional side view of the tissue retractor member of FIG. 7 showing a pin or screw that may be used with the retractor.

The engaging member 80 may be a pin, screw, or other structure or member associated with the retractor member 71 that provides threadable engagement between the threads 92 of the cannula 90 and the retractor member 71. Preferably, the engaging member is a ball tip screw 80 as shown in FIGS. 11 and 12. A threaded hole 73 (see, e.g., FIGS. 8, 9, and 13) is provided in the side surface 78 of the retractor member 71 to receive the ball tip screw 80. The screw 80 has external threads 84 for engaging the threaded hole 73 of the retractor member 71. Threaded hole 75 extends completely through the side surface 78 of the retractor member 1 and communicates with the central opening 75. Screw 80 has a conical end 82 terminating in a preferably rounded tip 83 for engaging the preferably rounded threads 92 of the cannula 90. The tip 83 of screw 80 acts as the mating thread for the threads 92 of the cannula 90. Accordingly, the screw 80 is preferably positioned in the threaded hole 73 so that the tip 83 of the screw protrudes into the central opening 75 of the retractor member 71 a sufficient amount to positively engage the threads 92 of the cannula 90. During the manufacturing of the retractor member 71, after screw 80 has been inserted to the desired depth in hole 73, the screw is preferably affixed permanently to the retractor member 71 to hold its position. Fabrication methods such as spot or tack welding, soldering, stacking, bonding, shrink fitting, etc. may be used to fix the screw 80 in position.

It should be noted that neither the engaging member, nor hole 75 need necessarily be threaded, and the invention is not limited in that regard. Accordingly, other embodiments may be used. For example, hole 75 could be unthreaded and an unthreaded pin or similar member could be used.

It should further be noted that the engaging member may be formed as an integral part of the retractor member. For example, in the embodiment shown in FIGS. 16–19, internal threads 121 may be formed in the central opening 122 of the retractor member 71 for engaging the threads 92 of the cannula 90, thereby eliminating the need for a threaded hole 73 and a separate engaging member such a ball tip screw or pin.

Referring again to FIGS. 11 and 12, the ball tip screw 80 has a tooling end 85 opposite the conical end 82 for engaging a screwdriver or other driver to insert the screw into the threaded hole 73 of the retractor member 71. A tool engagement recess, such as slot 81 as shown, is provided to engage the driver. Although a slot 81 is preferably provided, the tool engagement recess may be some other shape such as, for example, a phillips head recess, hex socket, etc.

As shown in FIG. 15, the cannula 90 and retractor member 71 may be used with an obturator 100 that has been inserted in the cannula 90. Such an obturator 100 preferably has conical end 101 with a blunt tip 114 (shown near distal end 93 of the cannula) that extends beyond the end of the cannula 90 when the obturator is fully inserted in the cannula. The obturator 100 may have a knob 113, which may be similar to the knob 112 of the cannula 90. The obturator 100 may be rotationally fixable in position in relation to the cannula 90 through a locking mechanism, such as the tab 103 and slot 104 arrangement as shown. With this arrangement, the cannula 90 may be rotated by turning the obturator knob 113.

Figure 20:
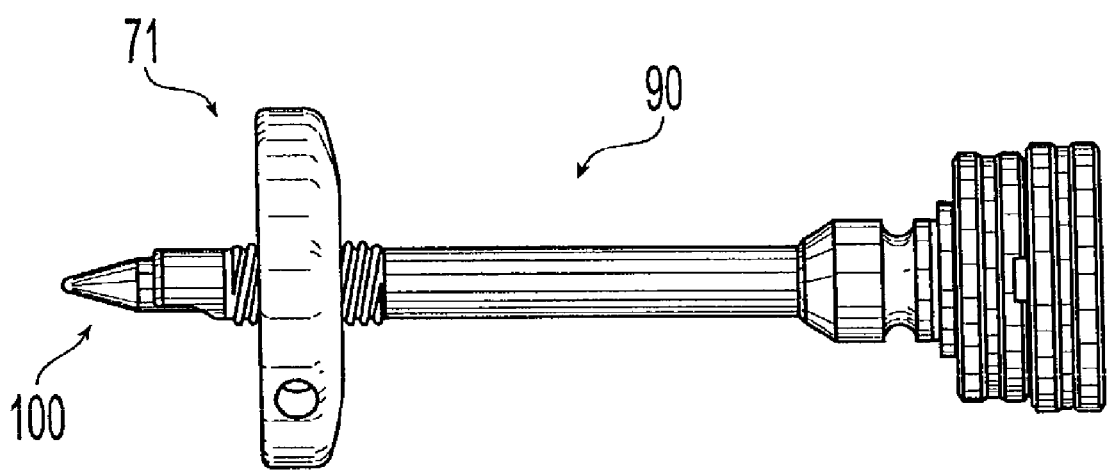
FIG. 20 is a side elevation view showing a tissue retractor member installed on the cannula of FIG. 14.

In a maxillofacial surgical procedure, the retractor member system may be operated by first inserting the cannula 90/obturator 100 combination (shown in FIG. 15) through a first bodily opening, such as an incision that has already been made through the cheek or other part of a patient. With the cannula 90/obturator 100 inserted, the retractor member 71, preferably held by a forceps, surgical pliers, or other tool, may be inserted through a second or other bodily opening and moved toward the cannula 90/obturator 100. For example, the retractor member 71 may be is inserted intra-orally through the open mouth of the patient. Alternatively, the retractor member 71 may be inserted through an opening or portal created by a second incision in the patient. Next, the central opening 75 of the retractor member 71 (through which ball tip screw 80 slightly protrudes) is aligned with and slid over the distal end 93 of the cannula 90/obturator 100 until resistance is met by the threaded portion 92 of the cannula 90. The cannula/obturator is then rotated via knobs 112 and/or 113, thereby engaging the retractor member 71 with the cannula 90. The cannula 90/obturator 100 is rotated until the surgeon achieves the desired degree of cheek retraction so that the cheek does not interfere with the surgical site procedures, such as drilling holes and inserting screws into the bone. FIG. 20 depicts the cannula 90/obturator 100 with the retractor member engaged thereon.

It should be noted that in lieu of rotating the cannula 90/obturator 100 to engage the retractor member 71, the cannula/obturator may be held stationary and the retractor member may be rotated to engage the retractor member with the cannula. Preferably, the cannula 90/obturator 100 is rotated and the retractor member 71 remains substantially stationary. Also preferably, the retractor member 71 is held With the cannula 90 remaining in place and near the surgical site on the bone, the obturator 100 may be withdrawn. Other surgical instruments and implants, such as drills and bone screws for example, may be inserted and used through the cannula 90 to complete the surgical procedure.

After the surgical procedure is completed, the retractor member 71 is once again grasped with a forceps or surgical pliers, and the cannula 90 is rotated to unscrew and remove the retractor member 71 from the cannula. The retractor member 71 is then retrieved from the patient through the second bodily opening.

Because either the retractor member or the cannula may be rotated to thread the retractor member onto the cannula, it will be apparent that a retractor member of any desired shape may be used. Accordingly, although a circular or ring-shaped retractor member is preferred, the retractor member may be configured to suite a particular type of surgical procedure.

It should be noted that although a maxillofacial surgical procedure has been described above, the retractor system may be used in any type of surgical procedure where tissue retraction is desired.

The handle including all of the forgoing components described (i.e., the cannula, obturator, drill guides, C-retractor, retractor member, etc.) may be constructed of any material suitable for use in surgical procedures. For example, the handle and its components may preferably be made of stainless steel which is commonly used; however, the invention is not limited in the type of materials employed which would be a matter of design choice.

It will be appreciated by those skilled in the art that the details of the handle and all of the foregoing components described herein are a matter of design choice, and that the invention is not limited to the particular embodiments or those features described. Accordingly, numerous modifications may be made to the handle and its components without departing from the spirit of the invention and scope of the claims appended hereto.

What is claimed is:

1. A system for retracting tissue, the system comprising: a cannula having an axial length, at least a portion of the cannula having external circumferential threads; and a retractor member having an opening configured to receive the cannula therethrough, internal threads associated with the opening, and an engaging member associated with and protruding at least partially into the opening for engaging the threads on the cannula, the retractor member adjustable along the axial length of the cannula.

2. The system of claim 1 further comprising a handle configured to releasably secure the cannula to the handle, the handle having a retractable slider pin for securing the cannula to the handle.

3. The system of claim 2 further comprising the cannula having a circumferential groove to engage the slider pin, the cannula capable of being rotated while being secured to the handle.

4. The system of claim 3 further comprising the handle having a handle lock assembly having a body with a top and a bottom, and an opening disposed in the handle body for receiving the cannula, the opening extending from the top to the bottom of the body, the retractable slider pin being movable from an extended position in which the pin protrudes into the opening to a retracted position in which the pin is withdrawn from the opening.

5. The system of claim 1 wherein the engaging member is a pin or screw protruding at least partially into the opening in the retractor.

6. A method of retracting tissue for a surgical procedure, the method comprising:
providing a cannula having a distal end and a proximal end;
providing a retractor member having an opening therethrough for receiving the cannula, the retractor member having an engaging member for engaging the cannula;
inserting the cannula through a first bodily opening;
inserting the retractor member through a second bodily opening;
guiding the distal end of the cannula into the opening of the retractor;

rotating the cannula or the retractor member to engage the retractor member and the cannula, whereby the tissue may be adjustably withdrawn from the distal end of the cannula.

7. The method of claim 6 wherein the retractor member and the cannula are rotatably engaged.

8. The method of claim 7 further comprising the cannula having an external surface with circumferential threads disposed on at least a portion of the external surface and the retractor member further comprises threads disposed on a surface of the retractor member surrounding the opening for receiving the cannula.

9. The method of claim 8 wherein the cannula is rotated to threadably engage the retractor member and the cannula.

10. The method of claim 9 wherein the retractor member is rotated to threadably engage the retractor and the cannula.

11. The method of claim 9 wherein the engaging member is a pin or screw having a tip protruding at least partially into the opening of the retractor.

12. The method of claim 6 wherein the first bodily opening is a first incision in the tissue of a patient and the second bodily opening is a second incision in the tissue of a patient.

13. The method of claim 6 wherein the first bodily opening is a first incision in the tissue of a patient and the second bodily opening is the mouth of a patient.

14. The method of claim 6 further comprising the step holding the retractor member in a substantially stationary position with a tool while the cannula is rotated to engage the retractor member.

15. A retractor kit comprising:
a cannula having external threads on at least a portion thereof;
a retractor member having an opening configured and adapted to receive the cannula, the retractor having an engaging member that is engageable with the external threads of the cannula;
a handle having a grasping portion and a handle lock assembly for holding the cannula;
wherein rotation of the cannula or the retractor member rotatably engages the retractor member with the cannula.

16. The kit of claim 15 further comprising an obturator that is configured and adapted to be inserted into the cannula.

17. A surgical retractor system comprising:
an elongated tubular member having external threads disposed on at least part of the tubular member; and
a retractor member having an opening configured and adapted to receive the tubular member, the retractor having an engaging member for engaging the tubular member, the engaging member has a blunted tip protruding at least partially into the opening of the retractor member for engaging the external threads of the tubular member;
wherein rotation of the tubular member or the retractor member rotatably engages the retractor with the tubular member, and wherein the external threads rotatably engage the engaging member of the retractor.

18. A surgical retractor system comprising:
an elongated tubular member having external threads disposed on at least part of the tubular member; and
a retractor member having an opening configured and adapted to receive the tubular member, the retractor having an engaging member for engaging the tubular member, the engaging member comprises a screw and the retractor member has a threaded hole communicating with the opening of the retractor member, the screw being disposed in the threaded hole;
wherein rotation of the tubular member or the retractor member rotatably engages the retractor with the tubular member, and wherein the external threads rotatably engage the engaging member of the retractor.

19. A surgical retractor system comprising:
an elongated tubular member; and
a retractor member having an opening configured and adapted to receive the tubular member, the retractor having:
at least one hole configured to engage at least part of a surgical instrument for manipulating the retractor member; and
an engaging member for engaging the tubular member;
wherein rotation of the tubular member or the retractor member rotatably engages the retractor with the tubular member.

20. A cheek retractor system comprising:
a cannula having threads disposed on at least a portion of the cannula;
a retractor member having an opening therethrough for receiving the cannula; and
an engaging member associated with the retractor member, the engaging member rotatably engaging the cannula;
wherein the engaging member is a screw having a tip, the tip of the screw protruding at least partially into the opening of the retractor for engaging the cannula.

21. A cheek retractor system comprising:
a cannula having threads disposed on at least a portion of the cannula;
a retractor member having a top surface, a bottom surface, a side surface, and at least one hole extending at least partially through the side surface for engaging part of a surgical instrument to manipulate the retractor member, and an opening therethrough for receiving the cannula; and
an engaging member associated with the retractor member, the engaging member rotatably engaging the cannula.

22. The system of claim 21 further comprising at least one hole extending from the top surface to the bottom surface of the retractor member for manipulating the retractor member.

23. A cheek retractor system comprising:
a cannula having threads disposed on at least a portion of the cannula;
a retractor member having an opening therethrough for receiving the cannula;
an engaging member associated with the retractor member, the engaging member rotatably engaging the cannula; and
at least two holes extending at least partially through the retractor member, the at least two holes each configured to receive part of a tool for manipulating the retractor member.

24. A cheek retractor system comprising:
a cannula having threads disposed on at least a portion of the cannula;
a retractor member having an opening therethrough for receiving the cannula; and
an engaging member associated with the retractor member, the engaging member rotatably engaging the cannula;
wherein the engaging member comprises a tip protruding at least partially into the retractor member opening.

25. The device of claim 24 wherein the engaging member is a screw that is threadably connected to the retractor member.

26. The device of claim 24 wherein the engaging member is a pin.

27. The device of claim 24 wherein the engaging member comprises threads disposed in the retractor opening.

28. A system for retracting tissue, the system comprising:
a cannula having an axial length, at least a portion of the cannula having external circumferential threads;
a retractor member having an opening configured to receive the cannula therethrough and an engaging member associated with and protruding at least partially into the opening for engaging the threads on the cannula, the retractor member adjustable along the axial length of the cannula; and
a handle configured to releasably secure the cannula to the handle, the handle having a retractable slider pin for securing the cannula to the handle.

29. The system of claim 28 further comprising the cannula having a circumferential groove to engage the slider pin, the cannula capable of being rotated while being secured to the handle.

30. The system of claim 29 further comprising the handle having a handle lock assembly having a body with a top and a bottom, and an opening disposed in the handle body for receiving the cannula, the opening extending from the top to the bottom of the body, the retractable slider pin being movable from an extended position in which the pin protrudes into the opening to a retracted position in which the pin is withdrawn from the opening.

31. The system of claim 28 wherein the engaging member is a pin or screw protruding at least partially into the opening in the retractor.

32. The system of claim 28 wherein the engaging member is formed by the retractor member having internal threads associated with the opening for receiving the cannula.

33. A system for retracting tissue, the system comprising:
a cannula having an axial length, at least a portion of the cannula having external circumferential threads; and
a retractor member having an opening configured to receive the cannula therethrough and an engaging member associated with and protruding at least partially into the opening for engaging the threads on the cannula, the retractor member adjustable along the axial length of the cannula;
wherein the engaging member comprises at least one of a pin and a screw protruding at least partially into the opening in the retractor.

34. The system of claim 33 further comprising a handle configured to releasably secure the cannula to the handle, the handle having a retractable slider pin for securing the cannula to the handle.

35. The system of claim 34 further comprising the cannula having a circumferential groove to engage the slider pin, the cannula capable of being rotated while being secured to the handle.

36. The system of claim 35 further comprising the handle having a handle lock assembly having a body with a top and a bottom, and an opening disposed in the handle body for receiving the cannula, the opening extending from the top to the bottom of the body, the retractable slider pin being movable from an extended position in which the pin protrudes into the opening to a retracted position in which the pin is withdrawn from the opening.

37. The system of claim 33 wherein the engaging member also comprises internal threads associated with the opening of the retractor member for receiving the cannula.

* * * * *